United States Patent
Jin et al.

(10) Patent No.: US 12,133,902 B2
(45) Date of Patent: Nov. 5, 2024

(54) DENTAL COMPOSITION

(71) Applicant: GC Corporation, Shizuoka (JP)

(72) Inventors: Satoshi Jin, Tokyo (JP); Takumasa Kimura, Tokyo (JP); Kyousuke Hirano, Tokyo (JP)

(73) Assignee: GC Corporation, Shizuoka (JP)

( * ) Notice: Subject to any disclaimer, the term of this patent is extended or adjusted under 35 U.S.C. 154(b) by 650 days.

(21) Appl. No.: 17/275,322

(22) PCT Filed: Apr. 22, 2019

(86) PCT No.: PCT/JP2019/017020
§ 371 (c)(1),
(2) Date: Mar. 11, 2021

(87) PCT Pub. No.: WO2020/066099
PCT Pub. Date: Apr. 2, 2020

(65) Prior Publication Data
US 2022/0047465 A1 Feb. 17, 2022

(30) Foreign Application Priority Data
Sep. 26, 2018 (JP) .................................. 2018-179878

(51) Int. Cl.
| | | |
|---|---|---|
| *A61K 6/887* | (2020.01) | |
| *A61K 6/16* | (2020.01) | |
| *A61K 6/20* | (2020.01) | |
| *A61K 6/30* | (2020.01) | |
| *A61K 6/66* | (2020.01) | |
| *C08L 33/10* | (2006.01) | |
| *C09D 133/06* | (2006.01) | |

(52) U.S. Cl.
CPC .............. *A61K 6/887* (2020.01); *A61K 6/16* (2020.01); *A61K 6/20* (2020.01); *A61K 6/30* (2020.01); *A61K 6/66* (2020.01); *C08L 33/10* (2013.01); *C09D 133/068* (2013.01)

(58) Field of Classification Search
CPC . A61K 6/887; A61K 6/66; A61K 6/16; A61K 6/20; A61K 6/30; C08L 33/10; C09D 133/068
See application file for complete search history.

(56) References Cited

U.S. PATENT DOCUMENTS

| | | | |
|---|---|---|---|
| 4,351,853 A | 9/1982 | Jochum et al. | |
| 5,160,737 A * | 11/1992 | Friedman ............... | A61K 9/006 |
| | | | 514/901 |
| 6,903,134 B2 | 6/2005 | Pflucker et al. | |
| 2003/0060426 A1 | 3/2003 | Pflucker et al. | |
| 2006/0241205 A1 | 10/2006 | Jia | |
| 2009/0176194 A1 | 7/2009 | Qian | |
| 2010/0311858 A1 | 12/2010 | Holmes et al. | |
| 2016/0081885 A1 | 3/2016 | Neffgen et al. | |

FOREIGN PATENT DOCUMENTS

| | | | |
|---|---|---|---|
| EP | 1323743 A2 * | 7/2003 | ................ C08F 2/44 |
| EP | 2077103 | 7/2009 | |
| JP | 2002-520347 | 7/2002 | |
| JP | 2003-524648 | 8/2003 | |
| JP | 2009-161533 | 7/2009 | |
| JP | 2011-502992 | 1/2011 | |
| JP | 2012-031155 | 2/2012 | |
| JP | 2013-133321 | 7/2013 | |
| JP | 2013-544823 | 12/2013 | |
| JP | 2014-015408 | 1/2014 | |
| JP | 2016-505525 | 2/2016 | |
| JP | 2016-166138 | 9/2016 | |
| JP | 2016-532640 | 10/2016 | |
| JP | 2017-141188 * | 8/2017 | |
| WO | 00/03688 | 1/2000 | |
| WO | 2012/071329 | 5/2012 | |
| WO | 2014/078537 | 5/2014 | |
| WO | 2015/051217 | 4/2015 | |
| WO | WO 2017/027774 * | 2/2017 | |

OTHER PUBLICATIONS

Machine English translation of JP 2014-015408, Akitsumi et al., Jan. 2014.*
Machine English translation of JP 2017-141188, Toriyabe et al., Aug. 2017.*
International Search Report for PCT/JP2019/017020 mailed on Jun. 11, 2019.

* cited by examiner

*Primary Examiner* — Patrick D Niland
(74) *Attorney, Agent, or Firm* — IPUSA, PLLC

(57) ABSTRACT

One embodiment of the present invention relates to a dental composition including a (meth)acrylate, an ultraviolet absorber, and a fluorescent agent, wherein the ultraviolet absorber has free of a maximum absorption wavelength in a range of greater than 320 nm and less than or equal to 500 nm.

1 Claim, No Drawings

DENTAL COMPOSITION

FIELD OF THE INVENTION

The present invention relates to a dental composition.

BACKGROUND OF THE INVENTION

In dental treatment, a paste-like photocurable composition commonly referred to as a composite resin is used to repair teeth damaged by caries, fractures, or the like.

It is demanded for the cured resin tooth of a composite resin to have aesthetic appearance similar to that of natural teeth. In addition to a high color matching of each patient's natural teeth with a cured resin tooth, it is also important for the composite resin to have high photostability so that there is minimal color change when the composite resin is exposed to ultraviolet light. In fact, it is required that color changes cannot be readily recognized by the naked eye when a cured resin tooth of a composite resin is exposed to sunlight for 10 hours in accordance with JIS T 6514.

Therefore, a benzotriazole compound is included as an ultraviolet absorber in the composite resin (see, for example, Patent Document 1).

In addition, a phthalate ester fluorescent agent is included in the composite resin (see, for example, Patent Document 1) because natural teeth absorb ultraviolet light and emit weak fluorescence.

In contrast, LED lights emitting a variety of colors have become familiar in recent years due to the development of LEDs. Near-ultraviolet light is less harmful to the human body than ultraviolet light. Therefore, near-ultraviolet LED light has increasingly used in medical practice.

RELATED-ART DOCUMENT

Patent Documents

Patent Document 1: Japanese Patent Application Laid-Open No. 2014-15408

SUMMARY OF THE INVENTION

Problems to be Solved by the Invention

A phthalate ester-based fluorescent agent absorbs ultraviolet light and near-ultraviolet light and emits fluorescent light. In contrast, a benzotriazole compound absorbs ultraviolet light in which the phthalate ester-based fluorescent agent absorbs, but does not absorb near-ultraviolet light in which the phthalate ester-based fluorescent agent absorbs. As a result, the benzotriazole compound inhibits the absorption of ultraviolet light by the phthalate ester-based fluorescent agent. Thus, even when the components of the composite resin are adjusted, a fluorescence of the cured resin tooth of the composite resin irradiated with either ultraviolet light or near-ultraviolet light to the cured resin tooth of the composite resin cannot be nearly equivalent to that of the natural teeth.

One aspect of the invention is to provide a dental composition that is excellent in photostability of a cured resin tooth and is capable of having a fluorescence of the cured resin tooth of the dental composition nearly equivalent to that of natural teeth upon emission of either ultraviolet light or near-ultraviolet light.

Means for Solving the Problems

One embodiment of the present invention relates to a dental composition including a (meth)acrylate, an ultraviolet absorber, and a fluorescent agent, wherein the ultraviolet absorber has free of a maximum absorption wavelength in the range of greater than 320 nm and less than or equal to 500 nm.

Effects of the Invention

According to one aspect of the present invention, a dental composition that is excellent in photostability of a cured resin tooth and is capable of having a fluorescence of the cured resin tooth of the dental composition nearly equivalent to that of natural teeth upon emission of either ultraviolet light or near-ultraviolet light.

DETAILED DESCRIPTION OF THE INVENTION

Next, an embodiment for carrying out the present invention will be described.

[Dental Compositions]

A dental composition of the present embodiment contains a (meth)acrylate, an ultraviolet absorber, and a fluorescence.

[(Meth)Acrylate]

In the present specification and claims, a (meth)acrylate refers to a compound (e.g., a monomer, an oligomer, a prepolymer, and the like) having a methacryloyloxy group or an acryloyloxy group (hereinafter referred to as (meth)acryloyloxy group).

The (meth)acrylate preferably has two or more (meth)acryloyloxy groups, and particularly preferably has two (meth)acryloyloxy groups.

The (meth)acrylate preferably has free of an acidic group.

Examples of (meth)acrylates free of an acidic group include methyl (meth)acrylate, ethyl (meth)acrylate, isopropyl (meth)acrylate, n-butyl (meth)acrylate, isobutyl (meth)acrylate, hydroxypropyl (meth) acrylate, tetrahydrofurfuryl (meth)acrylate, glycidyl (meth)acrylate, 2-hydroxyethyl (meth) acrylate, 2-hydroxypropyl (meth)acrylate, 3-hydroxypropyl (meth)acrylate, 2-ethoxyethyl (meth) acrylate, 2-methoxyethyl (meth) acrylate, 2-ethylhexyl (meth)acrylate, benzyl (meth)acrylate, 2-hydroxy-1,3-di(meth)acryloyloxypropane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylol methane tri(meth)acrylate, pentaerythritol tetra(meth)acrylate, polybutylene glycol di(meth)acrylate, ethoxylated bisphenol-A di(meth)acrylate, and bisphenol-A diglycidyl(meth)acrylate.

The (meth)acrylate may be used alone or as a combination of two or more kinds.

The content of (meth)acrylate in the dental composition of the present embodiment is preferably from 0.5 to 70% by mass and further preferably from 10 to 60% by mass. When the content of the (meth)acrylate in the dental composition of the present embodiment is 0.5% by mass or more, adhesion of the dental composition improves. When the content of the (meth)acrylate in the dental composition of the present embodiment is 70% by mass or less, the content of other components can be secured, thereby improving the performance of the dental composition.

[Ultraviolet Absorber]

An ultraviolet absorber has a maximum absorption wavelength in the ultraviolet region, but has free of a maximum absorption wavelength in the range of greater than 320 nm and less than or equal to 500 nm. This makes it difficult to inhibit the absorption of the fluorescent agent even when the cured resin tooth of the dental composition of the present embodiment is irradiated with either ultraviolet light or near-ultraviolet light. As a result, the fluorescence of the cured resin tooth of the dental composition is nearly equivalent to that of natural teeth.

The ultraviolet absorber preferably has a maximum absorption wavelength in the range of greater than 250 nm and less than or equal to 320 nm. This further improves the photostability of the cured resin tooth of the dental composition of the present embodiment.

Further, it is preferred that the ultraviolet absorber does not have a maximum absorption wavelength in the range of greater than 500 nm and less than or equal to 700 nm. Thus, this makes it even more difficult to inhibit the absorption of the fluorescent agent even when the cured resin tooth of the dental composition of the present embodiment is irradiated with either ultraviolet light or near-ultraviolet light. As a result, the fluorescence of the cured resin tooth of the dental composition becomes close to the fluorescence of natural teeth.

A preferred ultraviolet absorber is a compound represented by the following general formula.

[Chemical Formula 1]

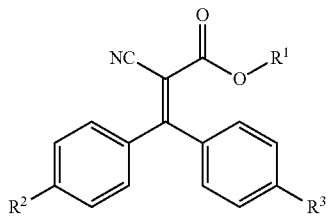

(1)

(In the formula, $R^1$ is a linear or branched chain alkyl group having 1 to 30 carbon atoms, and $R^2$ and $R^3$ are each independently hydrogen atoms, a linear or branched chain alkyl groups having 1 to 30 carbon atoms, or a linear or branched chain alkoxy groups having 1 to 30 carbon atoms.)

Examples of the alkyl groups in $R^1$, $R^2$, and $R^3$ include a methyl group, ethyl group, 2-ethylhexyl group, and the like.

Examples of the alkoxy group in $R^2$ and $R^3$ include a methoxy group, an ethoxy group, a 2-ethylhexyloxy group, and the like.

Examples of the compounds represented by the general formula (1) include a methyl 2-cyano-3,3-diphenylacrylate, ethyl 2-cyano-3,3-diphenylacrylate, 2-cyano-3,3-diphenylacrylate, and the like.

Examples of ultraviolet absorbers other than the compounds represented by the general formula (1) include a 2-ethylhexyl 4-(dimethylamino)benzoate, 4-aminobenzoic acid, and the like.

The ultraviolet absorber may be used alone or as a combination of two or more kinds.

The content of the ultraviolet absorber in the dental composition of the present embodiment is preferably 0.001 to 30% by mass and further preferably 0.1 to 10% by mass with respect to the (meth)acrylate. When the content of the ultraviolet absorber in the dental composition of the present embodiment is 0.001% by mass or more with respect to the (meth)acrylate, the photostability of the cured resin tooth of the dental composition further improves. When the content of the ultraviolet absorber in the dental composition of the present embodiment is 30% by mass or less, the photocurability of the dental composition improves.

[Fluorescent Agent]

A preferred fluorescent agent is a compound represented by the following general formula.

[Chemical Formula 2]

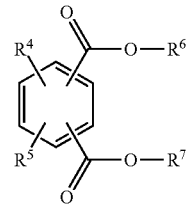

(2)

(In the formula, $R^4$ and $R^5$ are hydrogen atoms, amino groups or hydroxyl groups, and $R^6$ and $R^7$ are each independently alkyl groups.)

Examples of the alkyl groups in $R^6$ and $R^7$ include a methyl group, an ethyl group, a n-propyl group, an isopropyl group, and the like. Among these, an alkyl group having 1 to 3 carbon atoms are preferably used and an alkyl group having 1 to 2 carbon atoms are further preferably used.

Examples of the compounds represented by the general formula (2) include dimethyl 2,5-dihydroxy terephthalate, diethyl 2,5-dihydroxy terephthalate, dimethyl 2,5-diamino terephthalate, diethyl 2,5-diamino terephthalate, and the like.

A fluorescent agent other than the compounds represented by general formula (2) include, for example, phthalic acid derivatives such as o-phthalaldehyde and the like.

The fluorescent agent may be used alone or as a combination of two or more kinds.

The content of the fluorescent agent in the dental composition of the present embodiment is preferably 0.0001 to 20% by mass and further preferably 0.0005 to 1% by mass with respect to the (meth)acrylate. When the content of the fluorescent agent in the dental composition of the present embodiment is 0.0001% by mass or more and 20% by mass or less with respect to the (meth)acrylate, the fluorescence of the cured resin tooth of the dental composition approaches the fluorescence of natural teeth.

[Other Components]

The dental composition of the present embodiment may further contain a filler, a photopolymerization initiator, a photopolymerization accelerator, and the like.

[Fillers]

Examples of the materials constituting the filler include silica, barium glass, fluoroaluminosilicate glass, and the like.

The filler may be surface treated with a silane coupling agent.

Examples of silane coupling agents include 3-glycidyloxytrimethoxysilane, 3-(meth)acryloyloxypropylmethyldimethoxysilane, 3-(meth)acryloyloxypropyltriethoxysilane, 3-(meth)acryloyloxypropylethyldiethoxysilane, 3-(meth)acryloyloxypropylmethyldiethyl diethoxysilane, 2-(meth)acryloyloxyethoxypropyltrimethoxysilane, and the like.

The filler may be used alone or as a combination of two or more kinds.

A median size in a number-based size of the filler is preferably 0.005 to 5 μm and more preferably 0.05 to 0.5 μm.

The content of the filler in the dental composition of the present embodiment is preferably 40 to 95% by mass and further preferably 60 to 80% by mass. When the content of the dental composition of the present embodiment is 40% by mass or more, the mechanical strength of the cured resin tooth of the dental composition improves. When the content of the dental composition of the present embodiment is 95% by mass or less, the working ability of the dental composition improves.

[Photopolymerization Initiator]

Examples of photopolymerization initiators include camphorquinone, benzyl, diacetyl, benzyl dimethyl ketal, benzyl diethyl ketal, benzyl bis(2-methoxyethyl)ketal, 4,4'-dimethyl(benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10, 10-dioxide, thioxanthone-10-dioxide, benzoin methyl ether, benzoin ethyl ether, isopropyl ether, benzoin isobutyl ether, benzophenone, bis(4-dimethylaminophenyl)ketone, 4,4'-bis(diethylamino)benzophenone, (2,4,6-trimethylbenzoyl)diphenylphosphine oxide (TPO), bis(2,4,6-trimethylbenzoyl)phenylphosphine oxide, and the like.

The photopolymerization initiator may be used alone or as a combination of two or more kinds.

The content of the photopolymerization initiator in the dental composition of the present embodiment is preferably 0.01 to 10% by mass and further preferably 0.1 to 5% by mass with respect to the (meth)acrylate. When the content of the photopolymerization initiator in the dental composition of the present embodiment is 0.01% by mass or more with respect to the (meth)acrylate, the photocurability of the dental composition improves. When the content of the photopolymerization initiator in the dental composition of the present embodiment is 10% by mass or less with respect to the (meth)acrylate, the photostability of the cured resin tooth of the dental composition further improves.

[Photopolymerization Accelerator]

Examples of photopolymerization accelerators include tertiary amines such as 4-(N,N-dimethylamino)ethylbenzoate, N,N-dimethyl-p-toluidine, triethanolamine, tolyl diethanolamine, 4-dimethylamino methylbenzoate, 4-dimethyl amino isoamylbenzoate; barbituric acid derivatives such as barbituric acid, 1,3-dimethyl barbituric acid, 1,3,5-trimethylbarbituric acid, 1,3,5-triethylbarbituric acid, 5-butylbarbituric acid, 1-benzyl-5-phenylbarbituraic acid, 1-cyclohexyl-5-ethylbarbituric acid, and the like.

The photopolymerization accelerator may be used alone or as a combination of two or more kinds.

The content of the photopolymerization accelerator in the dental composition of the present embodiment is preferably 0.01 to 10% by mass and further preferably 0.1 to 5% by mass with respect to the (meth)acrylate. When the content of the photopolymerization accelerator in the dental composition of the present embodiment is 0.01% by mass or more with respect to the (meth)acrylate, the photocurability of the dental composition improves. When the content of the photopolymerization accelerator in the dental composition of the present embodiment is 10% by mass or less, the photostability of the cured resin tooth of the dental composition further improves.

[Form and Use of Dental Composition]

The dental compositions of the present embodiment may be provided in the form of, for example, liquids, pastes, and the like.

The dental compositions of the present embodiments include dental composite resins, dental adhesive filler materials, dental adhesives, dental milling resin materials, and the like.

EXAMPLES

Hereinafter, examples of the present invention will be described, but the present invention is not limited to the described examples.

Examples 1 to 9, Comparative Examples 1 to 3

Bis-GMA (60 parts by mass), 3G (20 parts by mass), and NPG (20 parts by mass) were mixed to obtain a monomer composition.

An ultraviolet absorber (predetermined amount), a fluorescent agent (predetermined amount), a filler (325 parts by mass), a photopolymerization initiator (0.2 parts by mass, and a photopolymerization accelerator (0.5 parts by mass) were added to the monomer composition (100 parts by mass). The mixture was kneaded to be a uniform paste in an agate mortar, and then defoamed under vacuum to obtain a paste-like composite resin.

Table 1 indicates the amount of the ultraviolet absorber and the fluorescent agent that are added.

Details of monomers, ultraviolet absorbers, fluorescent agents, fillers, photopolymerization initiators, and photopolymerization accelerators are as follows.

Monomers
Bis-GMA: Bisphenol A diglycidyl methacrylate
3G: Triethylene glycol dimethacrylate
NPG: Neopentylglycol dimethacrylate
Ultraviolet Absorbers
CDFA: Uvinul3039 (manufactured by BASF) (2-cyano-3,3-diphenylacrylic acid 2-ethylhexyl)
DMABA: 4-(dimethylamino) 2-ethylhexyl benzoate
BT: Tinuvin P (manufactured by BASF) (2-(2-hydroxy-5-methylphenyl)benzotriazole)
Fluorescent agent: Lumilux Blue LZ (manufactured by Honeywell) (diethyl 2,5-dihydroxyterephthalate)
Fillers: Fluoroaluminosilicate glass fillers surface-treated with 0.4 μm median size of 3-glycidyloxytrimethoxysilane in a number-based
Photopolymerization initiator: (±)-camphorquinone
Photopolymerization accelerator: 4-(N,N-dimethylamino) ethylbenzoate (DMABE)

[Fluorescence of Cured Resin Tooth of Composite Resin]

The composite resin was filled in the shape of central incisor and then exposed to light for 20 seconds using a photopolymerization illuminator G-Light Prima (manufactured by GC) to obtain a cured resin tooth of tooth-shaped composite resin.

The cured resin tooth of composite resin and a natural tooth were placed side by side. The cured resin tooth and the natural tooth were then irradiated by a fluorescent lamp and a near-ultraviolet LED light with ultraviolet light at wavelength of 365 nm and with near-ultraviolet light at 405 nm, respectively. The fluorescence of the cured resin tooth of composite resin was evaluated by observing the comparison of the fluorescence states of the cured resin tooth of composite resin and that of natural tooth. The evaluation criteria for the fluorescence of the cured resin tooth of the composite resin are as follows.

Excellent: The fluorescence state of the cured resin tooth of the composite resin is nearly equivalent to that of the natural tooth.

Good: The fluorescence state of the cured resin tooth of the composite resin is slightly poorer than that of the natural tooth, but there is no problem in use.

Poor: The fluorescence state of the cured resin tooth of the composite resin is inferior to that of the natural tooth, and there is a problem in use.

[Photostability of Cured Resin Tooth of Composite Resin]

A composite resin was filled in a ring-shaped mold with a diameter of 15 mm and a thickness of 1 mm and then pressed into contact with a polypropylene film. Then, the surface and the back surface of the ring-shaped mold was irradiated with UV light by a photopolymerization illuminator G-light prima (manufactured by GC) at nine locations via a glass plate for 10 seconds to obtain a cured resin tooth of the composite resin (test piece). The test piece was removed from the ring-shaped mold and stored in a dry, dark place at 37° C. for 24 hours.

Half of the test piece was covered with aluminum foil, then placed in an optical chamber and immersed in water at 37° C. and irradiated with ultraviolet light for 24 hours using a standard xenon white light source with an illumination intensity of 150,000 lux. At this time, the water level was maintained at 10±3 mm above the test piece. Then, the test piece that had been removed from the aluminum foil was stored in a dry dark place at 37° C. for 5 days. The color of the non-exposed and exposed portions of the test piece were measured using a colorimeter (manufactured by Minolta Co., Ltd.). The color difference $\Delta E^*$ was calculated from the following formulae, and the photostability of the test piece was evaluated.

$$\Delta E^* = \{(\Delta L^*)^2 + (\Delta a^*)^2 + (\Delta b^*)^2\}^{1/2}$$

$$\Delta L^* = L1^* - L2^*$$

$$\Delta a^* = a1^* - a2^*$$

$$\Delta b^* = b1^* - b2^*$$

$L1^*$ is the lightness index of the non-exposed portion of the test piece, and $a1^*$ and $b1^*$ are the metric chroma index of the non-exposed portion of the test piece. $L2^*$ is the lightness index of the exposed portion of the test piece, and $a2^*$ and $b2^*$ are the metric chroma index of the exposed portion of the test piece.

TABLE 1

| | Amount added [parts by mass] | | | | Fluorescence | | |
|---|---|---|---|---|---|---|---|
| | CDFA | DMABA | BT | Fluorescent agent | Ultraviolet light | Near-ultraviolet light | Photostability $\Delta E$ |
| Example 1 | 0.1 | — | — | 0.006 | Excellent | Excellent | 1.96 |
| Example 2 | 0.3 | — | — | 0.006 | Excellent | Excellent | 1.62 |
| Example 3 | 0.5 | — | — | 0.006 | Excellent | Excellent | 1.43 |
| Example 4 | 0.8 | — | — | 0.006 | Excellent | Excellent | 1.33 |
| Example 5 | 1.0 | — | — | 0.006 | Excellent | Excellent | 1.20 |
| Example 6 | 0.3 | — | — | 0.003 | Good | Good | 1.55 |
| Example 7 | 0.3 | — | — | 0.009 | Good | Good | 1.64 |
| Example 8 | 0.3 | — | — | 0.012 | Good | Good | 1.72 |
| Example 9 | — | 0.3 | — | 0.006 | Excellent | Excellent | 1.98 |
| Comparative Example 1 | — | — | 0.1 | 0.028 | Good | Poor | 1.84 |
| Comparative Example 2 | — | — | 0.1 | 0.006 | Poor | Excellent | 1.23 |
| Comparative Example 3 | — | — | 0.3 | 0.083 | Excellent | Poor | 1.19 |

From Table 1, the cured resin teeth of the composite resins of Examples 1 to 9 were irradiated with either an ultraviolet light or a near-ultraviolet light, the fluorescence of the cured resin teeth were nearly equivalent with the fluorescence of the natural tooth or slightly poor than that the natural tooth. Also, the photostability of the cured resin teeth were excellent.

In contrast, the fluorescence of the cured resin tooth of the composite resins in Comparative Examples 1 to 3 resulted in poor fluorescence than that of the natural tooth when either an ultraviolet light and a near-ultraviolet light emitted to the composite resin, because the composite resins contained BT with maximum absorption wavelength at 340 nm as the ultraviolet absorber.

This international application is based on and claims priority of Japanese Patent Application No. 2018-179878 filed Sep. 26, 2018, the entire contents of which are hereby incorporated by reference.

The invention claimed is:

1. A dental composition comprising:
    a (meth)acrylate;
    an ultraviolet absorber; and
    a fluorescent agent,
    wherein the ultraviolet absorber has a maximum absorption wavelength outside a range of greater than 320 nm and less than or equal to 500 nm, and
    wherein the ultraviolet absorber is at least one of 2-ethylhexyl 2-cyano-3,3- diphenylacrylate or 2-ethylhexyl 4-(dimethylamino) benzoate.

* * * * *